United States Patent [19]

Hoffman, Jr.

[11] Patent Number: 4,496,737

[45] Date of Patent: Jan. 29, 1985

[54] PROCESS FOR PREPARING SULFAMYLAMIDINE ANTISECRETORY AGENTS

[75] Inventor: Jacob M. Hoffman, Jr., North Wales, Pa.

[73] Assignee: Merck & Co., Inc., Rahway, N.J.

[21] Appl. No.: 432,219

[22] Filed: Sep. 27, 1982

[51] Int. Cl.$^3$ ............... C07D 277/42; C07D 307/52
[52] U.S. Cl. ................... 548/193; 546/332; 548/125; 548/131; 548/143; 548/205; 548/342; 549/491
[58] Field of Search ............ 546/332; 549/491; 548/131, 205, 342; 548/125, 143, 193

[56] References Cited

U.S. PATENT DOCUMENTS 4,379,158  4/1983  Hirata ................................. 424/273
4,382,090  5/1983  Pioch ................................. 424/270

OTHER PUBLICATIONS

March, Advanced Org. Chem., 2nd Ed., pp. 933-934, (1977).
Derwent Abstract 22898 E/12 of Japanese patent application No. 100,284.
Derwent Abstract 22901 E/12 of Japanese patent application No. 100,285.
Derwent Abstract 22902 E/12 of Japanese patent application No. 100,889.

*Primary Examiner*—Robert Gerstl
*Attorney, Agent, or Firm*—Gabriel Lopez; Salvatore C. Mitri; Hesna J. Pfeiffer

[57] ABSTRACT

A process is disclosed for preparing intermediates which are useful for obtaining sulfamylamidine antisecretory agents.

5 Claims, No Drawings

PROCESS FOR PREPARING SULFAMYLAMIDINE ANTISECRETORY AGENTS

SUMMARY OF THE INVENTION

This invention relates to a novel process for obtaining sulfamylamidine antisecretory agents.

The sulfamylamidine compounds which are useful as antisecretory agents and processes for preparing such compounds are disclosed and described in Japanese patent application Ser. No. JP 100,284 (Derwent Abstract 22898 E/12), Japanese patent application Ser. No. 100,285 (Derwent Abstract 22901 E/12), and Japanese patent application Ser. No. 100,889 (Derwent Abstract 22902 E/12).

The process of this invention differs from those disclosed in the aforementioned Japanese patent applications in that the heterocyclic component can be attached to sulfamylamidine synthon compounds to directly prepare desired end-product antisecretory agents without the need for a total synthesis.

DETAILED DESCRIPTION OF THE INVENTION

The process of this invention is directed toward preparing intermediates useful for obtaining sulfamylamidine compounds having the general formula:

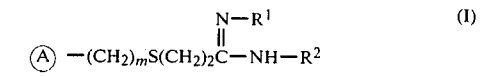

wherein:
- Ⓐ is a 5- or 6-membered heterocycle which can be optionally substituted by loweralkyl, di-loweralkylamino loweralkyl, N,N-di-loweralkylhydrazino, or guanidino;
- $R^1$ is sulfamyl or substituted sulfamyl wherein the substituent is aralkyl or aryl;
- $R^2$ is H or loweralkyl; and,
- m is 1–3.

The heterocyclic groups represented by A include rings such as, for example, pyridyl, imidazolyl, furanyl, thiazolyl, oxadiazolyl, and the like.

The loweralkyl groups, except where noted otherwise, represented by any of the variables include straight and branched chain hydrocarbon radicals of from one to six carbon atoms such as, for example, methyl, ethyl, propyl, isopropyl, butyl, isobutyl, t-butyl, pentyl, isopentyl, hexyl or vinyl, allyl, butenyl, and the like. The aralkyl groups represented by any of the above variables have from one to four carbon atoms in the alkyl portion thereof and include, for example, benzyl, p-methoxybenzyl, and the like Aryl where it appears in any of the radicals, except where noted, represents phenyl, or substituted phenyl wherein the substituents are alkyl, loweralkyl, alkoxy or halo.

The process of the invention is illustrated in the following Reaction Scheme wherein preferred reactants are shown to more clearly illustrate the process of the invention.

REACTION SCHEME

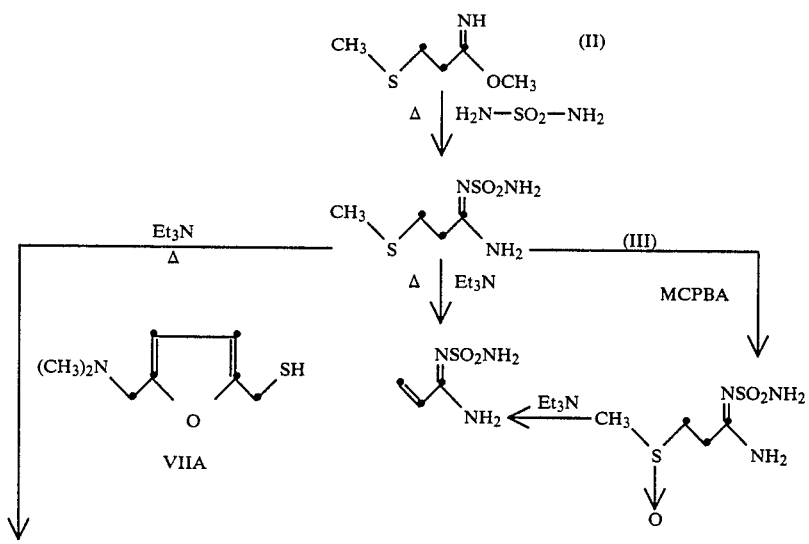

-continued
REACTION SCHEME

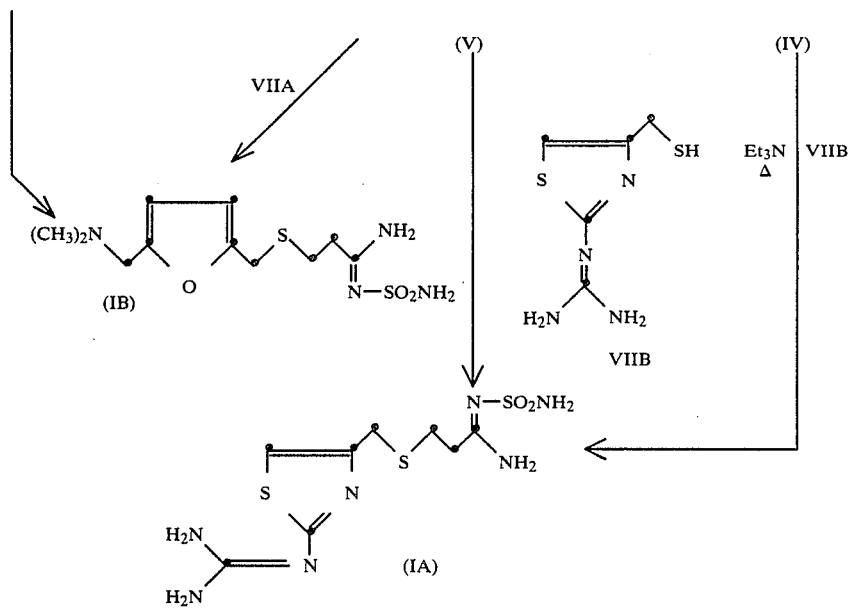

With reference to the Reaction Scheme, alkylimidate (II), which can be prepared from 3-(methylthio)proprionitrile by reaction with an alcohol such as methanol and hydrogen chloride gas, was reacted with a sulfamide in a refluxing alcohol solvent over a period of 20-40 hours to obtain sulfide (III). Peracid oxidation of sulfide (III) in a 1:1 mixture of methanol and chloroform with a peracid such as m-chloroperbenzoic acid or peracetic acid over a period of 30 minutes to 5 hours at 0° to 50° C., preferable at room temperature, afforded sulfoxide (IV).

Reacting sulfide (III) or sulfoxide (IV), preferably in refluxing ethanol, in the presence of a slight molar excess of a hindered amine base such as a tertiary amine, for example triethylamine, over a period of ½ to 3 days produced N-sulfamylacrylamidine (V). Reaction of the N-sulfamylacrylamidine (V) with a heterocyclic component having the structure: Ⓐ -(CH₂)ₘSH (VII), wherein Ⓐ and m are as defined above, yields sulfamylamidine (I). The reaction was carried out in a solvent such as methanol, dimethylformamide, or ethyl acetate, at from 0° C. to room temperature for a period of one minute to four hours. In most instances, however, the reaction is complete within about 5 minutes.

Alternatively, heterocycle component (VII) can be reacted with sulfide (III) or sulfoxide (IV) in the presence of a tertiary amine base as described above to obtain sulfamylamidine (I). The reaction is preferably carried out in a solvent such as ethanol or dimethylformamide at temperatures of about room temperature to the boiling point of the solvent, preferably about 80° C., for a period of 10 hours to 3 days.

The following Examples are provided to further illustrate the invention, but they are not to be construed as being limitative of the invention. Unless otherwise indicated, all temperatures are in degrees Celsius.

EXAMPLE 1
N-sulfamylacrylamidine

A suspension of N-sulfamyl-3-(methylsulfinyl)propionamidine (5.0 g, 23.5 mmol) in ethanol (100 ml) containing triethylamine (3.6 ml) was refluxed for 20-40 hours. Upon cooling, suspended solids were removed by filtration and the solvent evaporated to give a residue (3.4 g) which was chromatographed on silica gel and eluted with 3-7% methanol/chloroform. Upon concentration of appropriate fractions, the title compound crystallized to give 1.3 g, mp 72°-75°.

EXAMPLE 2
N-Sulfamyl-3-(methylsulfinyl)propionamidine

A solution of commercial 80% pure m-chloroperbenzoic acid (5.4 g, 25 mmol) in chloroform (40 ml) was added dropwise to a solution of N-sulfamyl-3-(methylthio)propionamidine (4.94 g, 25 mmol) in methanol (50 ml) at room temperature. After stirring for two hours, the product was collected by filtration, analytically pure, to give 4.44 g, mp 141°-144°.

EXAMPLE 3
N-Sulfamyl-3-(methylthio)propionamidine

A solution of sulfamide (22.0 g, 0.23 mol) in methanol (250 ml) was added dropwise to a refluxing solution of freshly prepared methyl 3-(methylthio) propionimidate (21.0 g, 0.158 mol) in methanol (175 ml) over a one hour period. After refluxing for an additional 20 hours, the reaction mixture was cooled, a slight precipitate was filtered off, and the solvent evaporated. The resultant residue was dissolved in methylene chloride (100 ml) and methanol (5 ml) from which unreacted sulfamide (10 g) crystallized and was removed by filtration. This solution was evaporated to give a residue (31 g) which was chromatographed on silica gel eluting with 5-8% methanol/chloroform. Upon concentration of the combined appropriate fractions, the product crystallized out to give 8.1 g, mp 88°–91°.

EXAMPLE 4

Methyl 3-(methylthio)propionimidate)

Hydrogen chloride gas was bubbled into a solution of 3-(methylthio) propionitrile (15.2 g, 0.15 mol) in chloroform (100 ml) containing methanol (28 ml), cooled in ice bath, for ¾ hour and then the solution was stoppered and refrigerated overnight. This solution was evaporated, the residue triturated with acetone, and the crystalline methyl 3-(methylthio)propionimidate hydrochloride (16.9 g) mp 100°–102°, collected by filtration. This salt was added to a solution of potassium carbonate (30 g) in water (200 ml) and the free imidate was extracted into 20% methanol/chloroform, dried over anhydrous sodium sulfate, and evaporated to give the title compound as an oil (13.4 g) which was used as is.

EXAMPLE 5

N-Sulfamyl-3-[(2-guanidinothiazol-4-yl)methylthio]-propionamide

To a solution of S-(2-guanidino-4-thiazolylmethyl-)isothiourea dihydrochloride (307 mg, 1.0 mmol) in methanol (5 ml) under a nitrogen atmosphere there was added 1.0 N sodium hydroxide (3 ml, 3.0 mmol). After stirring for ½ hour, a solution of N-sulfamyl acrylamidine (169 mg, 1.0 mol) in methanol (3 ml) was added. There was an instantaneous reaction to give product as indicated by TLC. After stirring for several hours, solvents were evaporated and the residue chromatographed on silica gel eluting with 10–15% methanol/chloroform to obtain pure product. When these fractions were combined and evaporated and the residue dissolved in a minimum amount of methanol and diluted with chloroform, the product slowly crystallized, 120 mg, mp 160°. A mixed melting point with authentic product was not depressed.

EXAMPLE 6

N-Sulfamyl-3-[(5-dimethylaminomethyl-2-furanyl)methylthio]propionamidine

To a solution of N-sulfamyl acrylamidine (340 mg, 2.0 mmol) in methanol (3 ml) there was added dropwise 5-(dimethylaminomethyl)furfurylthiol (340 mg, 2.0 mmol) in methanol (1 ml). The formation of product was instantaneous as indicated by TLC. After stirring for several hours, solvent was evaporated and the residue chromatographed on silica gel eluting with 3–8% methanol/chloroform. Upon concentration of the appropriate fractions, the title compound was obtained as an oil (370 mg).

Alternative procedure: To a suspension of N-sulfamyl-3-(methylthio)propionamidine (400 mg, 2.0 mmol) in ethanol (5 ml) there was added 5-(dimethylaminomethyl)furfurylthiol (345 mg, 2.0 mmol) and triethylamine (0.3 ml, 2.1 mmol) and the resulting mixture was refluxed for 3 days. Upon cooling, the solvent was evaporated and the residue chromatographed on silica gel eluting with 3–8% methanol/chloroform to give the title compound (40 mg).

What is claimed is:

1. A process for preparing a compound having the formula:

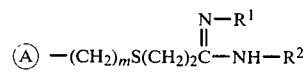

wherein:
- Ⓐ is a 5- or 6-membered heterocycle selected from the group consisting of pyridyl, imidazolyl, furanyl, thiazolyl, and oxadiazolyl, which can be optionally substituted by loweralkyl, di-loweralkylamino loweralkyl, N,N-di-loweralkylhydrazino, or guanidino;
- $R^1$ is sulfamoyl or substituted sulfamoyl wherein the substituent is (aralkyl or aryl:) phenyl, substituted phenyl, phenalkyl, or substituted phenalkyl, wherein the alkyl is of 1–4 carbons and the substituents are alkyl, loweralkyl, alkoxy, or halo;
- $R^2$ is H or loweralkyl; and
- m is 1–3;

said process comprising:

(a) reacting an alkylimidate having the formula:

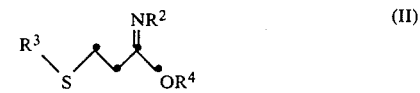

wherein $R^2$ is as defined above and $R^3$ and $R^4$ are independently alkyl, aryl or aralkyl, with a sulfamide to obtain a sulfide having the formula:

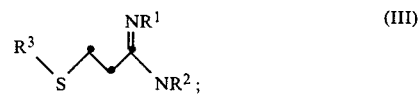

wherein $R^1$, $R^2$ and $R^3$ are as defined above;

(b) subjecting said sulfide (III) to peracid oxidation to obtain a sulfoxide having the formula:

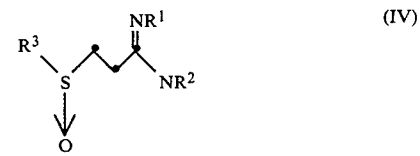

wherein $R^1$, $R^2$ and $R^3$ are as defined above;

(c) reacting said sulfide (III) or said sulfoxide (IV) in the presence of a hindered amine base to obtain an N-sulfamylacrylamidine having the formula:

wherein $R^1$ and $R^2$ are as defined above; and, (d) reacting said N-sulfamylacrylamidine (V) with a heterocycle compound having the formula:

wherein A and m are as defined above, to obtain said Formula I compound.

2. The process of claim 1 wherein said heterocycle compound (VII) has the formula:

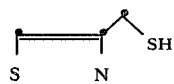

(VIIB)

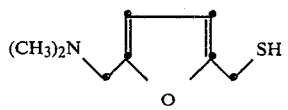

(VIIA)

and the Formula I compound obtained has the formula:

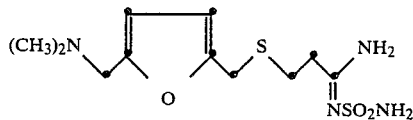

(IB)

and the formula I compound obtained has the formula:

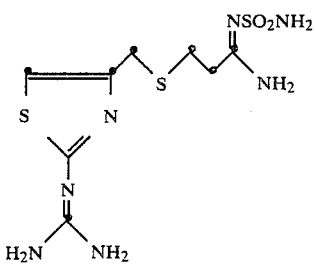

(IA)

4. The process of claim 1 wherein said heterocycle compound (VII) is reacted with said sulfide (III) or said sulfoxide (IV) in the presence of a hindered amine base to obtain said Formula I compound.

5. The process of claim 4 wherein said heterocycle compound (VII) has the formula:

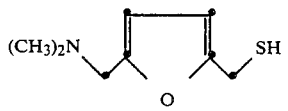

(VIIA)

and the Formula I compound obtained has the formula:

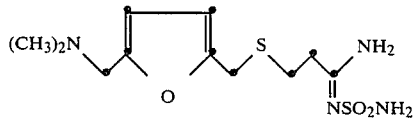

(IB)

3. The process of claim 1 wherein said heterocycle compound (VII) has the formula:

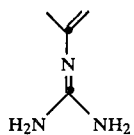

* * * * *